United States Patent [19]

Haglöf

[11] Patent Number: 4,584,769

[45] Date of Patent: Apr. 29, 1986

[54] EXTRACTOR FOR INCREMENT BORER

[75] Inventor: Ingvar Haglöf, Långsele, Sweden

[73] Assignee: Ingenjorsfirman I. Hagloff AB, Solleftea, Sweden

[21] Appl. No.: 468,990

[22] Filed: Feb. 23, 1983

[30] Foreign Application Priority Data

Feb. 25, 1982 [SE] Sweden ................................ 8201186

[51] Int. Cl.[4] ............................................. G01N 1/04
[52] U.S. Cl. .................................... 30/130; 73/864.44;
403/370; 403/371
[58] Field of Search ....................... 30/316, 113.1, 121,
30/337, 339, 342, 128, 130; 16/114 R, 114 A;
145/61 C, 61 F, 61 EA; 73/864.44, 864.45;
408/204; 403/370, 371

[56] References Cited

U.S. PATENT DOCUMENTS

| 961,475 | 6/1910 | Bacon | 403/371 |
|---|---|---|---|
| 1,323,619 | 12/1919 | Curtin | 30/342 |
| 2,737,704 | 3/1956 | Cinocca | 30/342 X |
| 4,329,882 | 5/1982 | Kaup . | |

Primary Examiner—Douglas D. Watts

Attorney, Agent, or Firm—Nies, Webner, Kurz & Bergert

[57] ABSTRACT

An extractor for an increment borer (1), which increment borer (1) consists of a tubular body having internally a cylindric portion, which transforms to a conic portion (6), and which on the outside is provided with bore threads (4). According to the invention, an end piece (10) is provided for being attached to and detached from the rearward end of the blade (9). The end piece comprises a sleeve (12) and a domed nut (14), each of which are provided with threads (13,15) arranged so, that the sleeve (12) and domed nut (14) are axially movable relative to another. The end piece (10) further comprises an oblong conic locking pin (16) intended to be inserted together with the rearward end of the blade (9) into an axial through hole in the sleeve (12). The domed nut (14) is intended at its threading on the sleeve (12) to axially move the locking pin (16), which thereby is pressed against the blade (9) located between the locking pin (16) and the wall of said hole of the sleeve (12).

The extractor comprises a known semitubular so-called blade (9).

2 Claims, 2 Drawing Figures

U.S. Patent    Apr. 29, 1986    4,584,769
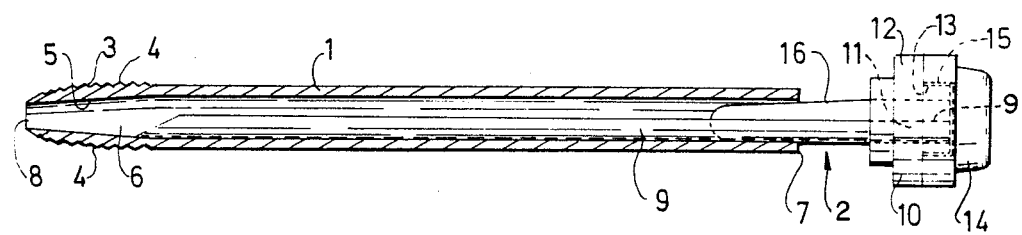
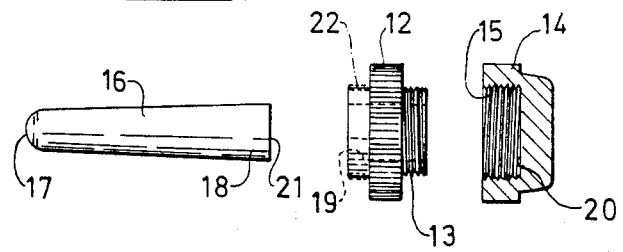

EXTRACTOR FOR INCREMENT BORER

This invention relates to a so-called extractor for an increment borer.

An increment borer is used for taking samples of trees. The sampling is carried out in such a manner, that an increment borer is driven in radial direction into the tree, whereafter the increment borer is screwed out. An increment borer consists of a tubular body, which is conically shaped at its forward end which is provided with external threads.

When the increment borer is being driven into a tree, a cylinder-shaped wood core, called an increment core, is pressed into the borer through an opening in the forward portion of the borer. For removing the increment core from the borer, an extractor is provided, which normally consists of an axially cleft tube, which is cleft along a diameter so that a tube half is formed. This extractor is inserted into the rearward end of the increment borer between the inner wall of the increment borer and the increment core while the increment borer is in the position after being driven into the tree. The increment borer thereafter is turned counterclockwise, i.e. it is screwed in an outward direction, through about one quarter of a revolution, whereby the increment core is turned off or broken from the tree at the forward portion of the increment borer. The extractor is provided at its forward portion with small barbs, which engage with the increment core when the extractor is being drawn out of the rearward end of the increment borer, whereby the increment core follows along resting on the semitubular portion of the extractor. The increment borer then is screwed out of the tree.

For some sampling of this type the increment core is studied and thereafter thrown away, or again inserted into the tree or stored.

The semitubular portion of the extractor, the so-called blade, is thin so that it can be inserted between the increment core and the inner wall of the increment borer. The blade, therefore, is readily deformed and easily damageable. During the working conditions prevailing in forests, it often occurs that somebody steps on a blade lying on the ground, or that the blade unintentionally is bent, which often results in that a new blade is required.

One reason why blades are deformed in use is because a great axial force may be required to be applied on the rearward portion of the blade in order to press the blade into the increment borer when the borer contains an increment core. In such cases the blade portion projecting outside the increment borer can be broken or bent.

Known blades are provided at their rearward end with an end knob, which is provided on its ouside with a thread so that the extractor on transport can be screwed onto the handle of the increment borer.

In view of the long walking distances in forests, often only one or a few extractors are taken along, because their weight in this connection is quite substantial, and because they require relatively much space.

The weight of the extractors to a great extent is due to the end knob.

The present invention solves the aforesaid shortcoming.

The present invention relates to an extractor for an increment borer, which consists of a tubular body having internally a cylindrical portion, which at its forward end transforms to a conic portion, which borer on its outer surface is provided with bore threads. The extractor includes a semitubular portion, a so-called blade. The extractor is characterized in that an end piece is provided for attachment to and detachment from the rearward end of the blade, including a sleeve and a domed nut, provided with co-operating threads arranged so that the sleeve and the domed nut can be fastened together and moved axially relative to one another. The extractor also includes an oblong locking pin of conic shape intended to be inserted together with the rear end of the blade into an axial through hole in the sleeve, and the domed nut is intended upon its being threaded onto the sleeve to axially move the locking pin, which thereby is pressed against the blade located between the locking pin and the wall of the hole in the sleeve.

The invention, provides that the extractor blade can be easily exchanged, so that a relatively great number of blades can be taken along, because the blades per se have a low weight and, besides, require little space when stacked one upon the other.

The invention is described in greater detail in the following, with reference to an embodiment of the invention shown in the accompanying drawing, in which FIG. 1 is an axial section of a conventional increment borer, into which an extractor according to the invention is inserted, and FIG. 2 is an exploded view of parts of the extractor.

In FIG. 1 is shown by way of an axial section a conventional increment borer 1, into which an extractor 2 according to the invention is partially inserted.

The increment borer 1 is of tubular shape and provided at its forward portion 3 with bore threads 4. The forward portion is slightly conic both on its outside 4 and inside 5. The conic portion 6 transforms to a cylindrical portion, which extends to the rearward end 7 of the increment borer.

The forward opening 8 of the increment borer has a diameter, which is smaller than the inner diameter of the cylindrical portion. The diameter of the forward opening 8 usually is 4.2 mm while the inner diameter of the cylindrical portion is 6.0 mm.

The extractor includes a well known semitubular portion, a so-called blade 9. According to the invention, an end piece 10 is intended to be attached to the rearward end 11 of the blade 9, as shown in FIG. 1.

In FIG. 1 the extractor is shown by way of a lateral view.

The end piece 10 comprises a sleeve 12 provided with external threads, and a domed nut 14 provided with internal threads 15. The domed nut 14 is intended to be threaded on the sleeve 12. The end piece 10 further comprises an locking pin 16, which preferably is made of a plastic material. The locking pin 16 is of elongated conic shape, so that its forward end 17 is rounded and has a smaller diameter than its rearward end 18.

The sleeve 12 is provided with a through hole 19, which has a slightly greater diameter than the locking pin 16. The domed nut 14 has internally a plane bottom 20.

For attaching an extractor blade 9 to the end piece 10, the rear end of a blade 9 is inserted into the sleeve 12. Thereafter the locking pin 16 is inserted into the sleeve from the right as viewed in FIG. 2, with its narrow end 17 first. The blade, thus, is now located between the surface of the locking pin 16 and the inner wall of the hole 19 of the sleeve 12. The conicity of the locking pin 16 is such that with only a slight pressure against its end surface 21 only a portion of the entire locking pin is pressed into the sleeve, and its rearward end 18 remains projected a short distance out of the sleeve 12. Thereafter the domed nut 14 is threaded on the sleeve 12 whereby its plane bottom 20 is abutted against and presses the locking pin substantially entirely into the sleeve 12. The blade 9 hereby is clamped between the locking pin and the inner wall of the sleeve 12. For removal of an increment core, the extractor blade is inserted into the increment borer, whereafter the blade is drawn out by pulling the end piece 10. When the blade 9 is to be exchanged, the domed nut 14 is loosened, whereafter the blade 9 and the locking pin 16 are pressed out of the sleeve, to the right in FIG. 2. Thereafter a new blade 9 is inserted, as described above.

The sleeve 12 may be provided on its outside with a thread 22, as shown by dashed line in FIG. 2, to render it possible to screw the sleeve on the handle of an increment borer or another transport receptacle.

According to a preferred embodiment, the locking pin 16 has such a length, that its forward end 17 projects into the increment borer 1 when the forward end of the blade 9 is located at the transition of said cylindric portion of the increment borer to said conic portion 6. The rearward portion of the blade 9, not yet in the borer body, is thus braced or supported so that its breaking is prevented even when a great axial force must be applied to the end piece 10 for pressing the forward portion of the blade 9 into the convergent inner portion 6 at the lead end of the increment borer.

By the present invention, thus, an extractor with rapidly and easily exchangeable blades is obtained.

The invention can be varied in several ways. The threads of the sleeve, for example, can be placed on the inside, and the threads of the domed nut can be placed on the outside. The locking pin, furthermore, can be formed with a portion coherent with the domed nut.

The invention, thus, must not be regarded restricted to the embodiments set forth above, but can be varied within the scope of the attached claims.

I claim:

1. An extractor in combination with an increment borer, the increment borer consisting of a tubular body having an internally cylindrical portion which, at its forward end, transforms to a convergent frusto-conical portion, the borer being provided on its outside with bore threads, said extractor comprising a semitubular blade and an end structure removably secured to the rearward end of the blade, said end structure comprising a sleeve with an axial through hole, a domed nut, and a locking pin each of said sleeve and said domed nut are provided with cooperating threads arranged so that said sleeve and said domed nut are axially movable and separable relative to one another, and said locking pin is elongated and essentially of conic shape and is inserted together with the rearward end of the blade into said axial hole in the sleeve, whereby said domed nut, upon being threaded on the sleeve, axially moves the locking pin, which is thereby pressed against the blade located between the locking pin and the wall of said axial hole in the sleeve to secure the rear end of the blade to said end structure.

2. An extractor and increment borer combination as defined in claim 1, characterized in that said locking pin has a length dimension enabling its forward end to project into the rear end of the increment borer when the blade has been partially inserted into the borer until its forward end is located at the transition of said cylindrical portion and said frusto-conical portion of the increment borer.

* * * * *